United States Patent [19]
Rhodes

[11] Patent Number: 5,995,873
[45] Date of Patent: Nov. 30, 1999

[54] TREATMENT OF PAIN AND OF THE NERVOUS SYSTEM

[76] Inventor: Donald A. Rhodes, 4833 S. Staples, Corpus Christi, Tex. 78411

[21] Appl. No.: 09/111,222

[22] Filed: Jul. 7, 1998

[51] Int. Cl.⁶ ..................................................... A61N 1/18
[52] U.S. Cl. .................................................................. 607/46
[58] Field of Search ................................. 607/67, 43, 46

[56] References Cited

U.S. PATENT DOCUMENTS

| | | |
|---|---|---|
| 4,292,980 | 10/1981 | Suzuki . |
| 4,830,009 | 5/1989 | Schmitt et al. ........................... 607/43 |
| 5,067,495 | 11/1991 | Brehm . |
| 5,417,719 | 5/1995 | Hull et al. ................................. 607/43 |
| 5,447,530 | 9/1995 | Guibert . |
| 5,458,625 | 10/1995 | Kendall . |
| 5,580,350 | 12/1996 | Guibert . |
| 5,643,329 | 7/1997 | Solomonow . |
| 5,817,138 | 10/1998 | Suzuki ...................................... 607/67 |
| 5,817,141 | 10/1998 | Iimori ....................................... 607/46 |

*Primary Examiner*—William E. Kamm
*Assistant Examiner*—George R. Evanisko
*Attorney, Agent, or Firm*—G. Turner Moller

[57] ABSTRACT

A method of treating pain and treating ailments associated with imbalances in the somatic and/or sympathetic nervous system includes delivering electricity through a circuit in the body. The circuit includes at least four nerves leading from at least two of the patient's extremities to various nerve roots adjacent the spinal column. Electrical energy from an electrical interferential therapy device is delivered though electrodes on the extremities adjacent the nerve endings. Patients report a reduction in pain and an improvement in objective and subjective symptoms suggesting some effect on the autonomic, particularly the sympathetic nervous system, and the somatic nervous system.

10 Claims, 3 Drawing Sheets

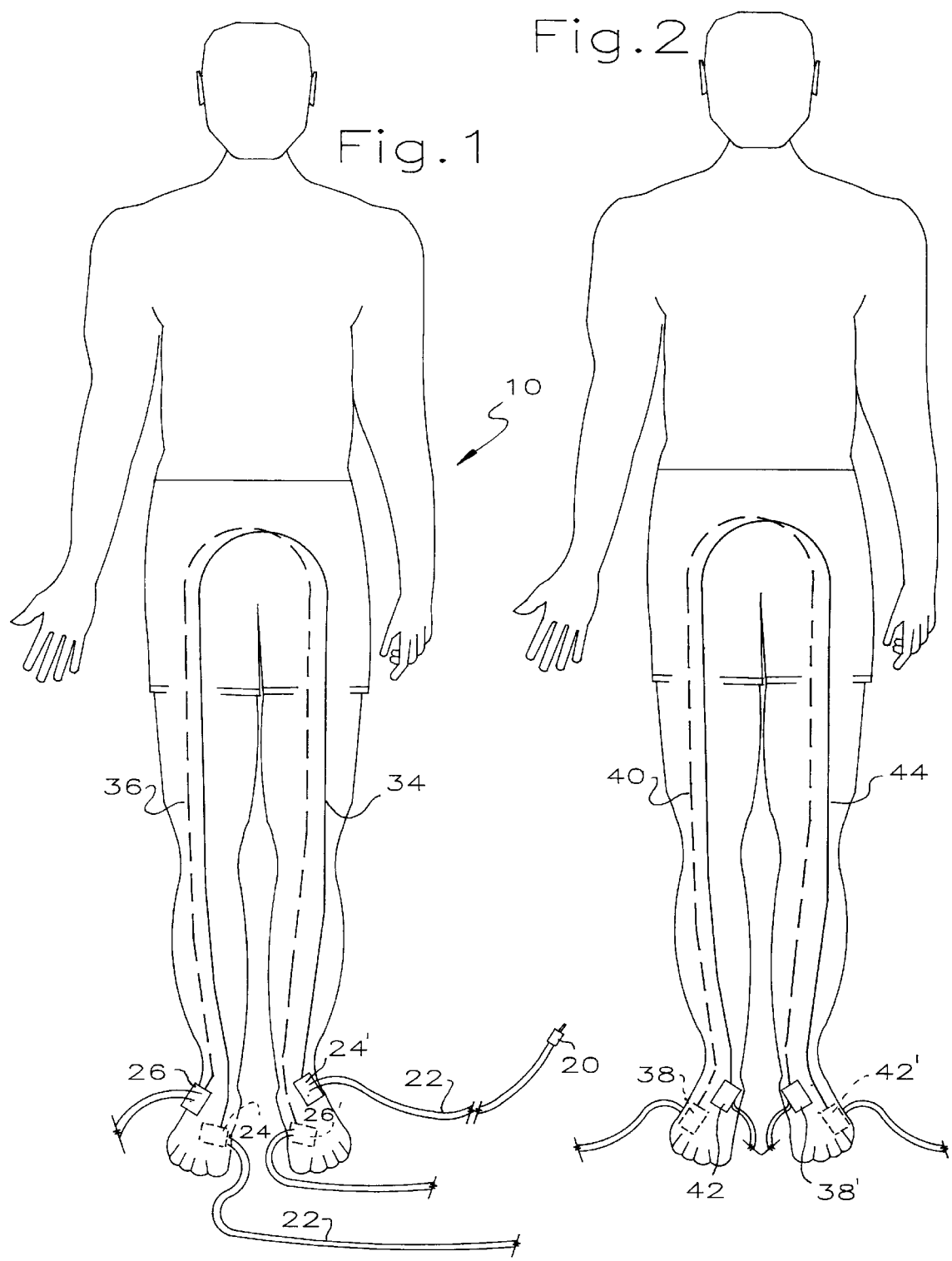

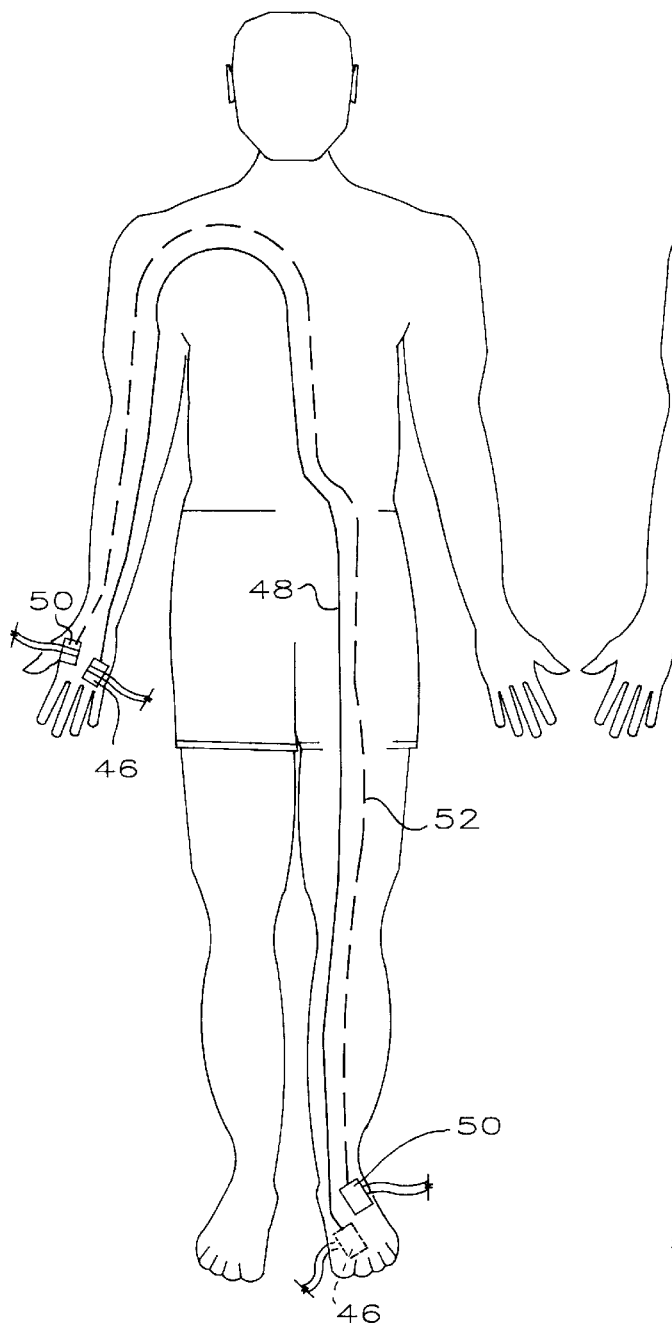
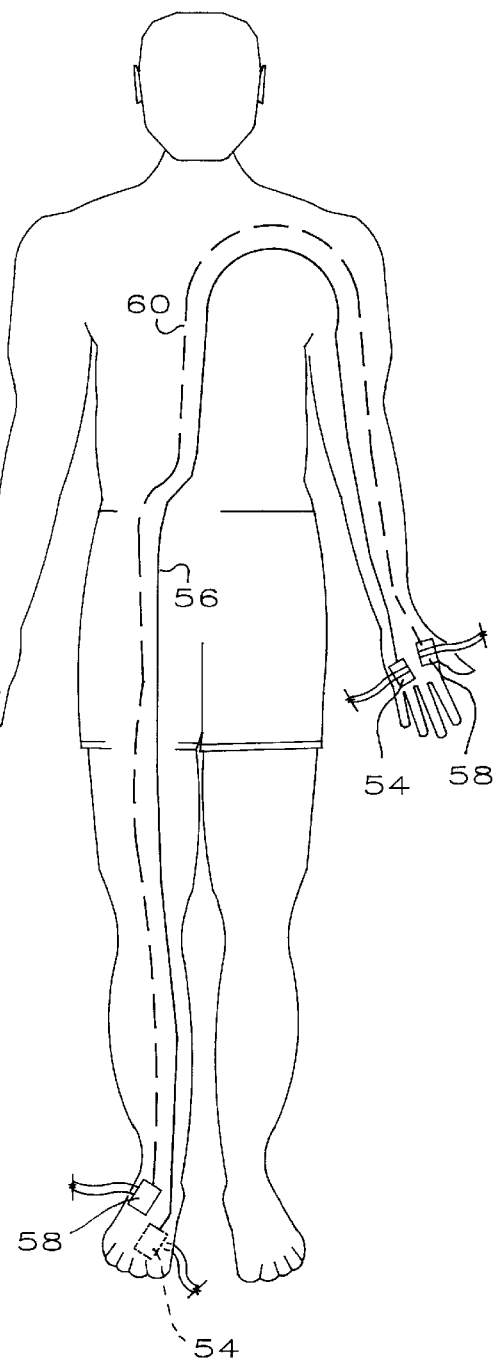

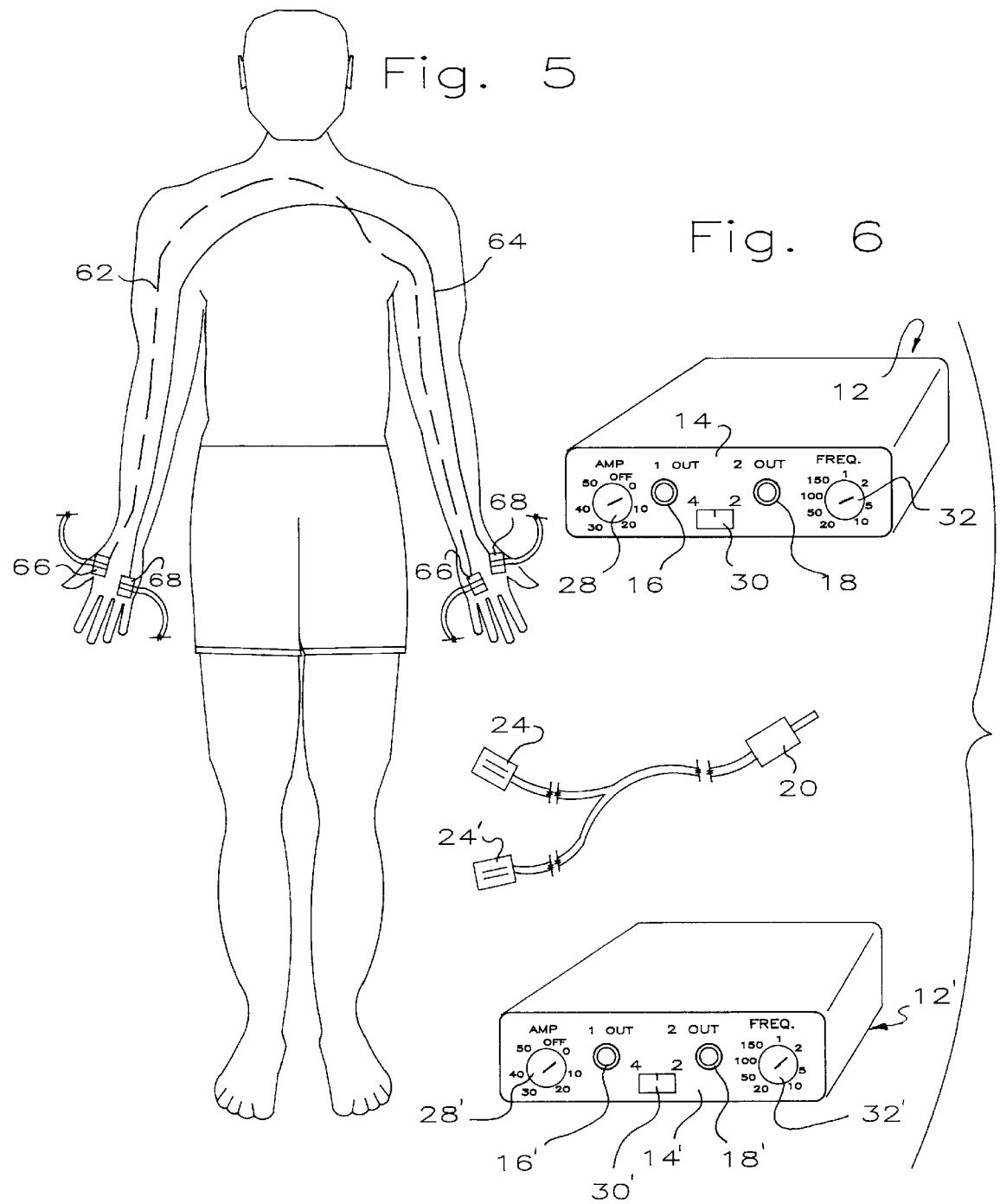

TREATMENT OF PAIN AND OF THE NERVOUS SYSTEM

This invention comprises a method of treating the human body and more particularly to treating the sympathetic nervous system and the somatic nervous system.

BACKGROUND OF THE INVENTION

It is well known in the art to treat pain or other symptoms by the application of energy in the form of alternating current electricity, magnetism and other forms of electromagnetic energy. One well accepted technique is known as electrical interferential therapy in which electrodes are connected in a crossing pattern adjacent the area to be treated. Alternating current is delivered through the electrodes into the body. One such device is commercially available from Rehabilicare Corporation of St. Paul, Minn. This type equipment is used to treat small areas of the body because the electrodes are spaced relatively close together in the region to be treated.

Disclosures of some interest are found in U.S. Pat. Nos. 4,292,980; 5,067,495; 5,447,530; 5,580,350; 5,458,625 and 5,643,329.

Modern animals, humans among them, have marvelously complex nervous systems. For purposes of analysis, the human nervous system is normally thought of as including a central nervous system consisting of the brain and spinal column, a peripheral nervous system consisting of twelve pair of cranial nerves and thirty one pairs of spinal nerves and an autonomic nervous system which helps regulate various organs and systems throughout the body. The autonomic nervous system has two main segments, the sympathetic or thoracolumbar system and the parasympathetic or craniosacral system. The nerves of the sympathetic nervous system arise in the thoracic and lumbar portions of the spinal cord. They run from the spinal cord to ganglia that lie along both sides of the spinal column. In the ganglia, the neurons from the spinal cord form a synapse with the neurons that continue to the various organs. As will be more fully apparent hereinafter, this invention acts primarily on the sympathetic or thoracolumbar nervous system and secondarily on the somatic nervous system and the central nervous system.

SUMMARY OF THE INVENTION

In this invention, patients are often selected who have not responded to more conventional treatment and who exhibit symptoms consistent with some imbalance typical of a poorly functioning sympathetic nervous system. One group of patients that has responded to this invention have, or have been diagnosed with, Reflex Sympathetic Dystrophy Syndrome, known by its acronym RSDS.

In this invention, energy is delivered through a circuit in the patient's body. The circuit includes nerves that extend from the extremities to the spinal column. Delivering energy, such as electricity with an electrical interferential device, through the circuit causes the electricity to pass through the nerve ganglia adjacent the spinal column which includes those mechanisms which control operation of the sympathetic nervous systems. While not being bound by any particular theory of operation, it appears that operation in accordance with this invention releases endorphins stored in some manner along the nerve path or adjacent the spinal column because there is a marked decrease in pain.

In addition to providing relief from pain, this invention promotes correction of the underlying imbalance in the sympathetic nervous system which lies at the cause of the ailment suffered by the patient. Again, without being bound by any particular theory, it appears that many of the successes of this invention can be explained by normalizing production and/or circulation of norepinephrine. Norepinephrine is a longer lasting version of epinephrine and both assist in transmitting nerve impulses and in constricting blood vessels. Overproduction of norepinephrine causes constriction of superficial small to medium arteries and arterioles which results in hypertension, trophic skin changes and demyelinization of nerves and hyperesthesia. Reducing the production and/or distribution of norepinephrine results in increased superficial arterial blood flow.

In one embodiment of the invention, electrical interferential equipment is used to deliver electrical energy along one nerve leading from one terminus on the hand or foot of the patient to the other terminus adjacent the nerve root adjacent the spinal column and along a second nerve leading from its terminus adjacent its nerve root adjacent the spinal column to its terminus on another hand or foot. In its traveling, the electrical energy alters and normalizes the sympathetic nervous system, which is controlled by the sympathetic ganglia which communicate with the spinal column through the same nerve roots as the electrical energy passes. This action has caused a reduction in pain perceived by the patient, as well as subjective and objective improvement in a number of observed conditions.

In summary, this invention comprises a method of treating a human for ailments related to the sympathetic nervous system comprising establishing a circuit in the human body including a first circuit path comprising a first nerve having a first terminus adjacent an extremity of the human and a second terminus adjacent a first spinal vertebra, a second nerve having a first terminus adjacent an extremity of the human and a second terminus adjacent a second spinal vertebra and a pathway between the second termini, and delivering electromagnetic energy through the circuit and through the pathway.

It is accordingly an object of this invention to provide an improved technique for treating patients suffering from pain.

Another object of this invention is to provide an improved method for treating patients by delivering electromagnetic energy through nerves leading from the spinal column to the extremities.

These and other objects and advantages of this description will become more apparent as this description proceeds, reference being made to the accompanying drawings and appended claims.

BRIEF DESCRIPTION OF THE DRAWINGS

FIG. 1 is a pictorial view of a patient showing, for clarity of illustration, part of the circuit established by practice of a first embodiment of this invention;

FIG. 2 is a pictorial view, similar to FIG. 1, showing the remainder of the circuit established by the first embodiment of this invention;

FIG. 3 is a pictorial view, similar to FIGS. 1 and 2, showing another circuit established by practice of a second embodiment of this invention;

FIG. 4 is a pictorial view showing another circuit established by practice of another embodiment of this invention;

FIG. 5 is a pictorial view showing another circuit established by practice of another embodiment of this invention; and FIG. 6 is a schematic view of a conventional electrical interferential therapy device.

DETAILED DESCRIPTION

In this invention, an electric circuit is established in the patient's body. The circuit includes at least two, often four and ideally eight segments. Each segment includes the nerve fibers having one terminus on an extremity, i.e. on the foot or hand of the patient, and one terminus adjacent a sympathetic nerve ganglia near a nerve ganglia adjacent a particular vertebra on the spinal column. Some type of electrical connection, the exact details of which are as yet unknown, is made between the nerve ganglia adjacent the spinal column. It is clear that the circuit includes the nerve fibers which extend from the more distal aspect of a first peripheral nerve to its root adjacent the spinal column. It is believed the circuit continues through the root of the first nerve into the spinal column, through the spinal column and exits from the spinal column through the root of a second nerve. The circuit continues through the fibers of the second peripheral nerve to a more distal aspect of that nerve.

The energy delivered through the circuit may be selected from a variety of electromagnetic types. Although interferential electrical energy has so far been shown to be the most desirable, H-wave stimulation with a physical therapy device such as made by Electronic Waveform Lab, Huntington Beach, Calif., galvanic stimulation with a physical therapy device such as a Model SW made by Rehabilicare Corporation, St. Paul, Minn., SMP stimulation with a physical therapy device which creates constantly changing TENS frequency such as made by Rehabilicare Corporation, St. Paul, Minn., or matrix electrostimulation with a physical therapy device such as made by Rehabilicare Corporation, St. Paul, Minn., have shown desirable effects.

Referring to FIGS. 1 and 6, a patient 10 is illustrated as being treated in accordance with this invention by a conventional electrical interferential therapy device 12 such as available commercially from Rehabilicare Corporation of St. Paul, Minn. The device 12 includes a control panel 14 with output jacks 16, 18 capable of accepting a jack 20 of an insulated wire pair 22 leading to electrode pairs 24, 24' and 26, 26'. The dial 28 of the device 12 controls the amplitude delivered to the electrodes and is set to deliver maximum amplitude consistent with patient comfort. The electrode switch 30 is set to either two or four depending on whether one or two pair of electrodes are being used. The setting of the frequency switch 32 is subject to some adjustment. The frequency switch 32 controls the "beat" frequency. For example, if the setting is at ten, the patient feels ten beats per second. In fact, the frequency of the alternating current delivered by the device of Rehabilicare is nominally 4000 Hz and the frequency switch 32 acts to vary the frequency, at a setting of ten, to 4010 Hz. In the event a more complete understanding of the device 12 is necessary, reference is made to appropriate publications of Rehabilicare Corporation. In this invention, the settings of the frequency switch 32 is normally below ten, and preferably below five and is optimally at four.

The electrodes 24, 26 are attached to the patient's skin in a conventional manner, i.e. they are self adherent. The location of the electrodes 24, 26 on the patient establish the electrical circuit in the patient's body. As shown in FIG. 1, in one technique, one electrode 24 is placed adjacent the end or terminus of the right medial plantar nerve L5 and its matching electrode or mate 24' is placed adjacent the end or terminus of the left sural nerve S1, inferior to the left ankle bone (lateral malleolus) thereby establishing or creating a first circuit 34 in the patient's body. As used herein, the reference characters L5, S1 and the like are standard medical terminology for the nerve. Those skilled in the art will recognize L5 as being the nerve which extends away from the fifth lumbar vertebra and S1 as being the nerve which extends away from the first sacral vertebra.

Those skilled in the art will recognize that the terminus of the right medial plantar nerve L5 is located on the bottom of the right foot, approximately on the ball of the foot. The terminus of the left sural nerve S1 is located below the left ankle bone (lateral malleolus). Another electrode 26 is placed adjacent the terminus of the right sural nerve S1 and its matching electrode or mate 26' is placed adjacent the terminus of the left medial plantar nerve L5 thereby establishing a second circuit 36 in the patient's body. Turning the device 12 on delivers electrical energy through the circuits 34, 36. Experience has shown a decrease in pain in patients complaining of pain and a decrease in symptoms consistent with an imbalanced sympathetic nervous system. Those skilled in the art will recognize that the medial plantar nerves L5 and the sural nerves S1 terminate adjacent the spinal column near adjacent spinal vertebra, in the area of the connection to the lumbar sympathetic ganglia.

Preferably, a second electrical interferential therapy device 12' is used simultaneously with the first device 12 and another set of circuits is simultaneously established as suggested in FIG. 2. The electrical interferential therapy device 12' is either a separate unit from the device 12 or they may be incorporated together in a single housing. In any event, an electrode 38 is attached to the patient's skin adjacent the terminus of the right lateral plantar nerve L5 and its matching electrode or mate 38' is placed adjacent the terminus of the left saphenous nerve L4, at the ankle, thereby establishing a circuit 40. Those skilled in the art will recognize that the terminus of the right lateral plantar nerve L5 is on the bottom of the right foot below the little toe and the fourth toe on the pad of the foot near the fifth metatarsal head. The terminus of the left saphenous nerve L4 is on the top inside (medial-anterior aspect) of the left ankle. An electrode 42 is attached to the patient's skin adjacent the terminus of the right saphenous nerve L4 and its matching electrode or mate 42' is placed adjacent the terminus of the left lateral plantar nerve L5 thereby establishing a circuit 44. Those skilled in the art will recognize that the terminus of the right saphenous nerve L4 is on the top inside of the right foot, forward of the right ankle. The terminus of the left lateral plantar nerve is on the bottom of the left foot below the little toe and the fourth toe on the pad of the foot. Turning the device 12 on delivers electrical energy through the circuits 40, 44. Experience has shown a decrease in pain in patient's complaining of pain and a decrease in symptoms consistent with an imbalanced sympathetic nervous system. The techniques of FIGS. 1 and 2 are preferably run simultaneously with similar or identical settings on the devices 12, 12'. Those skilled in the art will recognize that the lateral plantar nerves L5 and the saphenous nerves L4 terminate adjacent the spinal column near adjacent spinal vertebrae.

Another technique is shown in FIG. 3. An electrode 46 is placed adjacent the end or terminus of the nerve L5 of the left forefoot plantar aspect. Its matching electrode or mate 46' is placed adjacent the end or terminus of the right cranial nerve C8 where the fifth finger joins the right hand thereby establishing or creating a first circuit 48 in the patient's body. Another electrode 50 is placed adjacent the terminus of the left sural nerve S1 on the lateral aspect of the left ankle and its matching electrode or mate 50' is placed adjacent the terminus of the right cranial nerve C6 where the thumb joins the hand thereby establishing a second circuit 52 in the patient's body. Turning the device 12 on delivers electrical energy through the circuits 48, 52. Experience has shown a decrease in pain in patients complaining of pain and a decrease in symptoms consistent with an imbalanced sympathetic nervous system. Those skilled in the art will recognize that the nerves L5 and the sural nerves S1 terminate adjacent the spinal column near adjacent spinal vertebra, in the area of the connection to the lumbar sympathetic ganglia while the nerves C6, C8 terminate adjacent the spinal column near spinal vertebrae that are far above the termini of the nerves L5, S1. A second electrical interferential therapy device 12' may be used simultaneously with the first device 12 and another set of circuits may simultaneously established as suggested in FIG. 4 so the circuits of FIGS. 3 and 4 are normally used together. An electrode 54 is attached to the patient's skin adjacent the terminus of the nerve L5 on the right forefoot planar aspect and its matching electrode or mate 54' is placed adjacent the terminus of the cranial nerve C8 on the left palmer surface where the fifth finger joins the hand thereby establishing a circuit 56 in the patient's body. An electrode 58 is attached to the patient's skin adjacent the terminus of the right sural nerve S1 and its matching electrode or mate 58' is placed on the left palmer surface adjacent the terminus of the left cranial nerve C6 thereby establishing a circuit 60. Turning the device 12' on delivers electrical energy through the circuits 56, 60. Experience has shown a decrease in pain in patient's complaining of pain and a decrease in symptoms consistent with an imbalanced sympathetic nervous system. The techniques of FIGS. 1 and 2 are preferably run simultaneously with similar or identical settings on the devices 12, 12'. Those skilled in the art will recognize that the nerves L5 and the sural nerves S1 terminate adjacent the spinal column near adjacent spinal vertebra, in the area of the connection to the lumbar sympathetic ganglia while the nerves C6, C8 terminate adjacent the spinal column near spinal vertebrae that are far above the termini of the nerves L5, S1.

Referring to FIG. 5, another set of circuits 62, 64 is established. An electrode 66 is adhesively placed at the terminus of the cranial nerve C8 on the left palmer surface where the fifth finger joins the hand and its matching electrode 66' is placed at the terminus of the cranial nerve C6 on the right palmer surface where the thumb joins the hand thereby establishing the circuit 62. An electrode 68 is attached adjacent the terminus of the cranial nerve C6 on the left palmar surface where the thumb joins the hand and its matching electrode or mate 68' is placed adjacent the terminus of the cranial nerve C8 on the right palmer surface where the fifth finger joins the hand thereby establishing the circuit 64. Experience has shown a decrease in pain in patient's complaining of pain and a decrease in symptoms consistent with an imbalanced sympathetic nervous system.

Case Study 1

A six year old Caucasian female presented gastrointestinal symptoms such as severe pain following ingestion of any type food. The patient had numerous testings and treatments, without success. She was tentative diagnosed with Crohn's disease. Following twenty minutes of interferential electrical therapy treatment with a Rehabilicare Corporation device with a maximum comfortable amplitude setting and a beat frequency setting of four, with eight electrodes as shown in a combination of FIGS. 1 and 2, the patient was pain free and was able to eat spicy Mexican food, the same evening, without complaint. The patient was treated with interferential electrical therapy, matrix electrostimulation and H-wave with the electrodes as shown in a combination of FIGS. 1 and 2, for several months but never again had gastrointestinal problems.

Case Study 2

A twenty eight year old Caucasian female presented with severe menstrual cramps, lower body pain and headache. Past medical history includes Raynaud's phenomenon, recurrent headaches, sinus infection and allergies. The patient was treated with electrical interferential treatment with a Rehabilicare Corporation device, with a maximum comfortable amplitude setting, a beat frequency setting of four and an eight electrode pattern in accordance with a combination of FIGS. 1 and 2. Immediately following treatment, the patient reported a total resolution of all symptoms.

Case Study 3

An eight year old Caucasian boy presented with a severe headache and a full blown bronchial asthma attack, with accompanying allergic symptoms. The patient was given two metered puffs of an Albuterol inhaler and treated by electrical interferential therapy with a Rehabilicare Corporation device, with a maximum comfortable amplitude setting, a beat frequency setting of four and an eight electrode pattern in accordance with a combination of FIGS. 3 and 4. Immediately following treatment, the patient reported total relief from all symptoms.

Case Study 4

A 54 year old female presented with the diagnosis of Chronic Fatigue Syndrome. The patient was experiencing extreme fatigue, sleeplessness and lethargy. The patent was treated, twice weekly, with two interferential machines of the Rehabilicare Corporation using a maximum comfortable amplitude setting, a beat frequency setting of four and an eight electrode pattern in accordance with a combination of FIGS. 1 and 2. After the first week of treatment, the patient had a markedly increased energy level.

Case Study 5

A 43 year old Caucasian female presented with the diagnosis of Reflex Sympathetic Dystrophy Syndrome of fifteen months duration, in spite of numerous treatments including lumbar sympathetic blocks and oral medicines. The right foot was severely inflamed and discolored. The left foot was moderately inflamed and discolored. The patient had not worn shoes, other than bedroom slippers, for many months. The patient was treated daily, with two interferential machines of the Rehabilicare Corporation, using a maximum comfortable amplitude setting, a beat frequency setting of four, and an eight electrode pattern in accordance with a combination of FIGS. 1 and 2. Following the first treatment, the patent was able to begin wearing a tennis shoe, on the left foot. Following three treatments, the patient was able to begin wearing a tennis shoe on the right foot. Prior to the treatments, the patient was taking six to eight Hydrocodone capsules every day for pain. After beginning therapy, the patient no longer required any medicine for pain, even aspirin or ADVIL. Pitting edema was present, on the first visit, which required more than one minute to disappear. By the second visit, the pitting edema was resolving and by the third visit, the pitting edema was no longer apparent.

Case Study 6

A twenty eight year old Caucasian female presented with extreme pain, in the right hand, due to first and second degree burns on the distal portion of the thumb, second, third and fourth fingers of the right hand, of forty five minutes duration. When seen, the patient was applying ice to help alleviate the pain. After twenty minutes of matrix treatment with a Rehabilicare Corporation device, with an electrode pattern as shown in FIG. 5, the pain was totally eliminated.

There have been situations where a patient has suffered pain through the somatic nervous system and treatment with this invention has alleviated the pain.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A method of treating a human for ailments related to the nervous system comprising
    establishing a first circuit in the human body comprising a first nerve having a first terminus adjacent a first extremity of the human and a second terminus adjacent a first spinal vertebra, a second nerve having a first terminus adjacent a second extremity, different from the first extremity, of the human and a second terminus adjacent a second spinal vertebra and a pathway between the second termini, the step of establishing the first circuit including attaching a first electrode to the extremity adjacent the first terminus of the first nerve and attaching a second electrode to the extremity adjacent the first terminus of the second nerve;
    establishing a second circuit in the human body comprising a third nerve having a first terminus adjacent a third extremity of the human and a second terminus adjacent a third spinal vertebra, a fourth nerve having a first terminus adjacent a fourth extremity of the human, different from the third extremity, and a second terminus adjacent a fourth spinal vertebra and a second pathway between the second termini, the first circuit being separate from the second circuit, the step of establishing the second circuit including attaching a third electrode to the extremity adjacent the first terminus of the third nerve and attaching a fourth electrode to the extremity adjacent the first terminus of the fourth nerve;
    establishing a third circuit in the human body comprising a fifth nerve having a first terminus adjacent a fifth extremity of the human and a second terminus adjacent a fifth spinal vertebra, a sixth nerve having a first terminus adjacent a sixth extremity of the human, different from the fifth extremity, and a second terminus adjacent a sixth spinal vertebra and a pathway between the second termini, the first circuit being separate from the second and third circuits, the step of establishing the third circuit including attaching a fifth electrode to the extremity adjacent the first terminus of the fifth nerve and attaching a sixth electrode to the extremity adjacent the first terminus of the sixth nerve;
    delivering electromagnetic energy through the circuits including delivering the electromagnetic energy through the first and second electrodes, through the third and fourth electrodes and through the fifth and sixth electrodes.

2. The method of claim 1 wherein the first and second vertebra adjoin one another.

3. The method of claim 1 wherein the first and second vertebra are spaced apart by at least one vertebra.

4. The method of claim 1 wherein the establishing step further comprises
    establishing a fourth circuit in the human body comprising a seventh nerve having a first terminus adjacent an extremity of the human and a second terminus adjacent a seventh spinal vertebra, an eighth nerve having a first terminus adjacent a different extremity of the human and a second terminus adjacent a eighth spinal vertebra and a pathway between the second termini, the first circuit being separate from the second, third and fourth circuits.

5. The method of claim 4 wherein the step of delivering electromagnetic energy through the circuit comprises delivering an interferential electrical signal.

6. The method of claim 5 wherein the step of delivering an interferential electrical signal includes delivering an interferential electrical signal having a beat frequency less than about ten.

7. The method of claim 5 wherein the step of delivering an interferential electrical signal includes delivering an interferential electrical signal having a beat frequency less than five.

8. The method of claim 5 wherein the step of delivering an interferential electrical signal includes delivering an interferential electrical signal having a beat frequency of four.

9. A method of treating a human for ailments related to the nervous system comprising establishing a circuit in the human body comprising a first nerve having a first terminus adjacent an extremity of the human and a second terminus adjacent a spinal vertebra, a second nerve having a first terminus adjacent a different extremity of the human and a second terminus adjacent a different spinal vertebra and a pathway between the second termini, the establishing step including attaching a first electrode to the extremity adjacent the first terminus of the first nerve and attaching a second electrode to the different extremity adjacent the first terminus of the second nerve; and delivering electromagnetic energy substantially only through the electrodes on the extremities and thereby through the circuit.

10. The method of claim 9 further comprising establishing a second circuit in the human body comprising
    a third nerve having a first terminus adjacent a third extremity of the human and a second terminus adjacent a third spinal vertebra,
    a fourth nerve having a first terminus adjacent a fourth extremity of the human, different from the third extremity, and a second terminus adjacent a fourth spinal vertebra, different from the third spinal vertebra, and
    a second pathway between the second termini, the first circuit being separate from the second circuit, the step of establishing the second circuit including attaching a third electrode to the extremity adjacent the first terminus of the third nerve and attaching a fourth electrode to the extremity adjacent the first terminus of the fourth nerve, and
    the delivering step comprising delivering electromagnetic contemporaneously into all of the electrodes and thereby contemporaneously through the circuits.

* * * * *